United States Patent [19]

Welzel et al.

[11] Patent Number: 5,055,295

[45] Date of Patent: Oct. 8, 1991

[54] LYSIS OF FIBRIN BLOOD CLOTS WITH UROKINASE AND PRO-UROKINASE

[75] Inventors: Dieter Welzel; Helmut Wolf, both of Nuremberg, Fed. Rep. of Germany

[73] Assignee: Vascular Laboratory, Inc., Boston, Mass.

[21] Appl. No.: 346,188

[22] Filed: May 2, 1989

Related U.S. Application Data

[63] Continuation of Ser. No. 103,989, Oct. 1, 1987, abandoned.

[30] Foreign Application Priority Data

Oct. 3, 1986 [GB] United Kingdom ............... 8623823

[51] Int. Cl.$^5$ .............................................. A61K 37/54
[52] U.S. Cl. ............................... 424/94.2; 424/94.63; 424/94.64; 435/215
[58] Field of Search ................. 424/94.2, 94.63, 94.64; 435/215

[56] References Cited

U.S. PATENT DOCUMENTS

| Re. 32,271 | 10/1986 | Husain et al. | 435/215 |
|---|---|---|---|
| 3,926,727 | 12/1975 | Vairel et al. | 424/94.63 |
| 4,286,063 | 8/1981 | Suyama | 435/215 |

OTHER PUBLICATIONS

Lijnen et al., *The Journal of Biological Chemistry*, vol. 261, No. 3, Jan. 25, 1986, pp. 1253-1258.
Wun et al., *The Journal of Biological Chemistry*, vol. 257, No. 12, Jun. 25, 1982, pp. 7262-7268.
Gurewich et al., *J. Clin. Invest.*, vol. 73, Jun. 1984, pp. 1731-1739.
Wun et al., *The Journal of Biological Chemistry*, vol. 260, No. 8, Apr. 25, 1985, pp. 5061-5066.
Collen et al., *Biological Abstracts*, vol. 79, No. 11, Abs. 98147, Jun. 1, 1985.
Collen et al., *Biological Abstracts*, vol. 80, No. 9, Abs. 79943, Nov. 1, 1985.
Van de Werf et al., *Biological Abstracts*, vol. 81, No. 12, Abs. 114481, Jun. 15, 1986.
Matsuo et al., *Biological Abstracts*, vol. 82, No. 2, No. 2, Abs. 16231, Jul. 15, 1986.
Gurewich et al., *Thrombosis Research*, vol. 44, No. 2, pp. 217-228, Jul. 1986.
Pannell et al., *Biological Abstracts*, vol. 82, No. 3, Abs. 30970, Aug. 1, 1986.
Conference Abstract, San Diego, Jul. 1985, 0722, (Gurewich et al.).
Conference Abstract, Paris, Oct. 1985, (Guerwich).
Conference Abstract, Los Angeles, Feb. 1986, E3, (Collen).
Conference Abstracts, Vienna, Aug. 25-29, 1986, 212, (Nguyen), 213, (Collen), 219, (Gurewich et al.) and 227 (Verstraete).
Gurewich, conference notes read at Jul. 1985, San Diego Conference, (see reference AR).

*Primary Examiner*—Jose G. Dees
*Assistant Examiner*—Vera C. Clarke
*Attorney, Agent, or Firm*—Fish & Richardson

[57] ABSTRACT

The thrombolytic effect of the plasminogen activator pro-urokinase is improved synergistically by the co-administration of urokinase. The two components may be administered sequentially or simultaneously, and if simultaneously, either separately or as a mixture. Preferably an initial bolus injection of urokinase is followed by an infusion of pro-urokinase.

9 Claims, No Drawings

LYSIS OF FIBRIN BLOOD CLOTS WITH UROKINASE AND PRO-UROKINASE

This application is a continuation of application Ser. No. 103,989, filed on Oct. 1, 1987, now abandoned.

Several naturally-occurring enzymes are known to participate in the lysis of fibrin clots, and have been used therapeutically to lyse clots in patients, e.g. coronary patients, in whom life-threatening clots have formed. Two of these enzymes are pro-urokinase (pro-UK) and urokinase (UK). UK is believed to be synthesized in vivo in a single-chain, zymogenic form (pro-UK) which is converted to the two-chain form (UK) by a proteolytic cleavage. An alternative name for pro-UK is single chain urinary plasminogen activator (scu-PA).

Both agents, UK and pro-UK, can be used for thrombolysis in early myocardial infarction in order to limit or even prevent definite myocardial necrosis. UK is used in dosages of more than 1 000 000 I.U. for this purpose, preferred intravenous dosages being 2 000 000 to 3 000 000 I.U. per application. The use of pro-UK for this indication is currently under investigation, and results so far show that dosages of above 6 500 000 I.U. are necessary in order to obtain good results.

The activities of pro-UK and UK were originally expected to be at best strictly additive. However, it has now been found that UK surprisingly has a synergistic effect on the therapeutic activity of pro-UK. In particular, when an initial bolus of UK is administered it is found that subsequent administration of pro-UK is much more effective, resulting in a dramatic reduction of the overall dosage required in order to achieve the beneficial therapeutic effect.

The subsequent administration of pro-UK must be within a time interval close enough to provide a synergistic effect. It should begin within 15 minutes, preferably 5 minutes, from the end of the administration of UK, and may last for up to approximately 60 minutes.

It has also been found that this synergistic effect is not confined to the case where initial administration of UK is followed by subsequent administration of pro-UK, but is also found when pro-UK is administered first, followed by UK; or when pro-UK and UK are administered simultaneously, whether by separate infusions or injections, by a single injection from a double-barrelled syringe, or by a single injection or infusion of a mixture of pro-UK and UK.

Accordingly, the invention now provides a method of lysing fibrin blood clots in patients in need of such treatment, comprising administration of an effective amount of a combination of UK and pro-UK, either simultaneously or sequentially such that the administration of the second component begins within 15 minutes from the end of the administration of the first component, each of UK and pro-UK being administered in effective or less than effective amounts.

Alternatively, the invention provides the use of UK together with pro-UK, in free or fixed combination, as a thrombolytic agent. As a further alternative, the invention provides the use of UK for the preparation of an agent for the potentiation of the thrombolytic effect of pro-UK.

By "synergistic effect" is meant a fibrin clot lysing activity greater (either in terms of increased rapidity of lysing or a greater amount of lysing, or both) than would be expected from the additive effect of the two active agents when administered independently.

Urokinase may be used in either the low molecular weight form (LMW-UK, MW ~33,000 daltons) or the high molecular weight form (HMW-UK, MW ~55,000 daltons), of which the HMW form is preferred. The UK may be obtained from natural sources (e.g. urine) or may be obtained by recombinant DNA techniques involving cleavage of the initially formed single-chain form (pro-UK), as reported by W. E. Holmes et al, Bio/Technology 3 923 (1985). HMW-UK is commercially available as Ukidan (R.T.M.) or Actosolv (R.T.M.), LMW-UK as Abbokinase (R.T.M.).

Similarly pro-UK may be obtained from urine as originally described in European Patent 40238, or from cultures of natural cell lines or cell lines transformed by recombinant DNA technology, and may be obtained in forms differing in degree of glycosylation or in other respects.

The pro-UK used according to this invention will normally be human pro-UK having the amino-acid sequence as shown for pro-UK in FIG. A of European Patent Application 92182, ignoring the lead sequence from $-20$ to $-1$. However, the pro-UK used in the invention may vary from this structure by substitution, deletion or addition at one or more amino acid residues, so long as it retains essentially the same biological activity. Thus for example a non-human pro-UK or a compound such as described in PCT patent application WO 86/04351, having a different amino acid substituted for lys-135 and/or phe-157 or as described in European Patent Application 200 451, having substitutions or deletions at phe-157 or lys-158 is within the definition of "pro-UK" so long as it retains biological activity. Furthermore, truncated forms of pro-UK for example such as described by Rijken et al in *Thrombosis Research* 42 749–760 and 761–768, are included in the definition of "pro-UK" so long as biological activity is retained. Such molecules may have their amino-terminal at lys-136, corresponding to single-chain LMW-UK, or at other convenient sites for example ala-132, lys-144 and glu-150. Forms of pro-UK having additional amino acids for example an initial methionine are also included if active.

The term "essentially the same biological activity" means that the molecule has at least 50% of the activity of normal human pro-UK as measured by the Gurewich et al assay disclosed infra, and the terms "active", "retains biological activity" and "biological activity is retained" are to be construed correspondingly.

The structure of human HMW-UK is that of pro-UK as described above in which the single amino-acid chain is cleaved between positions 158 and 159. The structure of human LMW-UK is that of HMW-UK in which the amino acids numbered 1–135 have been lost. As described above for PUK, the UK used in the invention may differ in corresponding manner from either of the two normal human UK molecules (HMW-UK and LMW-UK) so long as it has at least 50% of the activity of normal UK as measured by the fibrin plate test described below.

Patients receiving particular benefit from the invention include post-operative patients, patients who have recently suffered myocardial infarction resulting from clots and patients suffering from deep vein thrombi. Pro-UK and UK, separately or together, are admixed with a pharmaceutically acceptable carrier substance, e.g. saline, and administered parenterally, either intravenously or by injection into affected arteries or the heart. Intravenous administration, which is preferred, may be by infusion, by a bolus injection, or by a combination of these.

Preferably, the patient also receives heparin, for example a bolus injection of 5000 I.U. heparin before administration of any PUK or UK, optionally followed by infusion of 1000 I.U./hr of heparin. The heparin may also be given in the form of a mixture with the pro-UK or the UK, or as a mixture of all three components.

The preferred quantity of UK used in the process according to the invention is from 100,000 I.U. to 300,000 I.U., more preferably from 150,000 I.U. to 250,000 I.U., particularly 200,000 I.U. The preferred quantity of pro-UK used is less than 6 500,000 I.U., more preferably from 2 000,000 I.U. to 4,000,000 I.U.

The above quantity of UK is most effective when administered as a bolus injection 15 minutes or less before administration of pro-UK. However, it may be preferred, for ease of administration, to administer a mixture of pro-UK and UK in a single injection or infusion, preferably as a single bolus injection. According to a further aspect of the invention, therefore, there is provided a pharmaceutical composition comprising a mixture of UK and pro-UK together with a pharmaceutically acceptable diluent or carrier, or a mixture of UK and pro-UK in pure lyophilised form.

The components of the synergistic mixture of the invention may also be presented in twin-pack form, that is, as a single package containing separate unit dosages of UK and pro-UK with instructions for concomitant administration.

Preferably the composition is substantially pure, that is, it contains no significant quantity of any pharmaceutically active material other than UK and pro-UK. More preferably the composition is analytically pure, that is, it contains no protein other than UK and pro-UK in a quantity detectable by analytical methods available at the date of this application. When a diluent or carrier is present, this is preferably sterile water for injection or sterile isotonic saline.

The weight ratio of UK to pro-UK in the composition according to the invention is preferably from 1:40 to 1:6.7, more preferably 1:20 to 1:10, particularly 1:15 to 1:10. Preferably the composition is made up in unit dosage forms e.g. vials for injection or bottles for infusion, each containing 100,000-300,000 I.U. of UK and 2,000,000-4,000,000 I.U. of pro-UK, more preferably 200,000 I.U. UK and 2,000,000-3,000,000 I.U. of pro-UK.

Such a unit dosage form contains a combined total dosage of UK and pro-UK of from 2,100,000 to 4,300,000 I.U., corresponding to approximately 21-43 mg of protein. The amounts of each compound are thus much lower than the amount of each required for optimal clot lysis when used in the absence of the other in the same therapeutic regimen.

According to a further aspect of the invention, the patient is given a bolus injection of UK and a bolus injection of pro-UK followed by an infusion of pro-UK. The amount of UK given as a bolus is as described above, i.e. preferably 100,000-300,000 I.U., more preferably 150,000-250,000 I.U., particularly 200,000 I.U. The amount of pro-UK given as a bolus is preferably 300,000-1,000,000 I.U., more preferably 400,000-600,000 I.U., particularly 500,000 I.U. These quantities may be administered as two separate bolus injections, delivered in any order, or from a twin-barrelled syringe; or as a single bolus injection of a mixture of UK and PUK, which represents a further composition according to the invention.

The weight ratio of UK to pro-UK in this composition is preferably from 1:10 to 1:1, more preferably 1:4 to 1:1.6, particularly 1:2.5. Preferably, however, the UK is administered before any pro-UK is given.

It may also be desirable to administer heparin together with the bolus of UK and/or pro-UK. The amount of heparin to be added to the above quantities of UK, pro-UK or UK/pro-UK mixture is preferably from 1000 to 10,000 I.U., more preferably about 5000 I.U.

The amount of pro-UK given as a subsequent infusion is preferably approximately 100,000 I.U./minute, which may be given for approx. 40 min., i.e. a total of 4,000,000 I.U. In many cases opening of the occluded artery may occur within 30 minutes or even less, and infusion may be stopped after this time if arterial opening is established for example by coronary angiography.

For use in this aspect of the invention, there is provided a kit comprising a unit dosage of UK for injection, a unit dose of pro-UK for injection, and a unit dose of pro-UK for infusion. The kit is preferably presented in a single package, and in association with instructions for administration. The unit dosage forms for injection may be sterile solutions of UK or pro-UK in pure water or in physiological saline, or may be in lyophilised or freeze dried solid form to which sterile water or saline is added before injection. The unit dosage form of pro-UK for infusion may be a solution in physiological saline or other sterile aqueous medium for infusion, or a lyophilised or freeze dried solid or a liquid concentrate from which an infusion solution can be made up. The solution for injection or infusion may contain other components, for example buffer salts such as $Na_2HPO_4/NaH_2PO_4$ and preservatives e.g. mannitol and human albumin, and these components may also be present in the lyophilised or freeze dried solid forms.

The quantity of UK and of pro-UK in the unit dosage forms for injection is preferably as described above, particularly 200,000 I.U. of UK and 500,000 I.U. of pro-UK; the quantity of pro-UK in the unit dosage form for infusion is preferably 3,000,000-5,000,000 I.U. more preferably 4,000,000 I.U.

The combination of low-dose UK (200,000 I.U.) and low-dose pro-UK (3 000 000 I.U.) can achieve effective thrombolysis in the majority of cases of myocardial infarction. To achieve the same rate of success with UK alone, dosages of 2,000,000 to 2,500,000 I.U. would be necessary, and at this dosage level side effects such as systemic fibrinogenolysis and loss of plasminogen are found. To achieve the same results with PUK alone, dosages well in excess of 6,500,000 I.U., for example 9,000,000 I.U. may be necessary. These results indicate a synergistic interaction between UK and pro-UK in clot lysis.

The quantity of each compound is expressed herein either by weight (mg) or in International Units (I.U.) based on the International Reference Preparation of UK assayed on a standard fibrin plate (Brakman, *Fibrinolysis, A standardized Fibrin Plate Method and a Fibrinolytic Assay of Plasminogen*, Scheltema & Holkema NV, Amsterdam, 1967, pp. 1-24). Pro-UK is assayed after activation by plasmin as described in: Gurewich et al., *J. Clin. Invest.* (1984) 73, pp. 1731-1739. UK (both HMW and LMW forms) and pro-UK gave similar specific activities (about 100 000 I.U./mg), so that protein concentrations could be compared (1 I.U. = 10 ng protein). Consequently, all weight ratios are also approximate I.U. ratios.

As UK is conveniently available in ampoules containing 250,000 I.U., a dosage of 250,000 I.U. of UK may be substituted for that of 200,000 I.U., wherever described in this Specification and Examples. Use of the 250,000 I.U. dose avoids the difficulty of estimating 4/5 of an ampoule, and gives the same beneficial effects as for the 200,000 I.U. dose.

EXAMPLE 1

A 58-year old woman suffering from myocardial infarction received a bolus injection of 200,000 I.U. of urokinase i.v. followed by a bolus injection of 1,000,000 I.U. prourokinase and an infusion of prourokinase at a rate of 5.5 million I.U./hr. Partial perfusion was attained after 15 minutes, and complete perfusion after 30 minutes, i.e. after a total of 3,250,000 I.U. of pro-UK had been administered. There was still complete perfusion 24 hours after administration.

EXAMPLE 2

A male patient suffering from myocardial infarction received a mixture of 200,000 I.U. urokinase and 2,500,000 I.U. of pro-UK infused over 15 minutes. Complete perfusion was obtained by the end of this period.

EXAMPLE 3

Dosage Forms a) Mixture for injection 200,000 I.U. UK and 2,000,000 I.U. pro-UK are dissolved in 20 ml sterile isotonic saline and packaged in a vial for injection.

b) Lyophilized mixture

A solution of 200,000 I.U. UK and 3,000,000 I.U. pro-UK is lyophilized and the solid residue sealed in a vial to which saline for injection can be added.

c) Twin-barrelled syringe

One barrel of the prepackaged syringe contains 200,000 I.U. UK in 10 ml sterile isotonic saline, the other contains 3,000,000 I.U. pro-UK in 10 ml sterile isotonic saline.

d) Twin-pack

A twin pack comprises one vial containing 200,000 I.U. UK in lyophilized form and one vial containing 3,000,000 I.U. pro-UK in lyophilized form, with instructions for concomitant administration.

EXAMPLE 4

The dosage forms of Example 3 are also made up using 500,000 I.U. pro-UK instead of 2,000,000 or 3,000,000 I.U. pro-UK.

EXAMPLE 5

In a multi-centre, open, prospective clinical trial, the following protocol was used:

Criteria for Inclusion 1) pain, characteristic for myocardial infarction, of at least 30 min. duration
2) onset of symptoms less than five hours before the start of lytic therapy
3) ECG findings characteristic of myocardial infarction
4) informed consent of patient.

Criteria for Exclusion 1) contra-indications for coronary angiography 2) contra-indications for lytic therapy
 a) commencement of therapy with heparin or coumarin
 b) venous or arterial puncture within the last 8 days
 c) cerebrovascular accident within the last two months
 d) active bleeding
 e) stomach or duodenal ulcer within the last year
 f) surgical operation within the last 8 days
 g) haemorragic diathesis
3) incomplete blockage of coronary artery (as shown by coronary angiography)
4) partial or complete reperfusion after administration of nitroglycerine
5) cardiac-related coma
6) serious heart valve- or heart disease, hypertrophic cardiomyopathy
7) serious kidney or liver disease, which could affect the excretion of pro-urokinase
8) use of oral contraceptives.

Procedure

Patients meeting the above critera for inclusion are given 5000 I.U. heparin, and a coronary angiography is carried out. If a total arterial blockage is observed, 100–200 ug nitroglycerine is given intracoronarily, and angiography of the blocked vessel is repeated. If no opening is observed after administration of nitroglycerine, the patient is given 200,000 I.U. high HMW-urokinase in an intravenous bolus injection, followed by 500,000 I.U. pro-urokinase i.v. in a bolus injection given over 3 minutes. Immediately thereafter intravenous infusion of 4,000,000 I.U. pro-UK is carried out over 40 minutes. Coronary angiography is carried out at 15 min. intervals to check the progress of clot lysis, and this is repeated 60 minutes after successful lysis, and also 24 hours and 3 weeks after treatment, to check for re-occlusion.

Results

Of 19 patients treated according to this protocol, 14 (74%) showed re-opening or patency of the occluded artery after the 40 minutes infusion. Of these, two showed re-occlusion after 24 hours.

We claim:

1. A method of lysing fibrin blood clots in patients in need of such treatment, comprising intravenous administration of an effective amount of a combination of UK and pro-UK, either simultaneously or sequentially such that the administration of the second component begins within 15 minutes from the end of the administration of the first component, each of UK and pro-UK being administered in effective or less than effective amounts.

2. The method according to claim 1 in which the dosage of UK is from 150,000 to 250,000 I.U. and the dosage of pro-UK is from 2,000,000 to 4,000,000 I.U.

3. The method according to claim 1 in which the UK is administered as a bolus injection prior to an injection or infusion of pro-UK.

4. A pharmaceutical composition for lysis of fibrin blood clots comprising a mixture of effective amounts of UK and pro-UK together with a pharmaceutically acceptable diluent or carrier, or a mixture of effective amounts of UK and pro-UK in pure lyophilized form.

5. A composition according to claim 4 in which the weight ratio of UK to pro-UK is from 1:40 to 1:6.7.

6. A unit dosage form of a composition according to claim 5 containing 2,000,000 I.U. UK and 2,000,000 to 3,000,000 I.U. pro-UK.

7. A composition according to claim 4 in which the weight ratio of UK to pro-UK is from 1:4 to 1:1.6.

8. A unit dosage form of a composition according to claim 7 containing 150,00-250,000 I.U. UK and 400,000-600,000 I.U. pro-UK.

9. A unit dosage form according to claim 8 containing additionally 1000 to 10,000 I.U. of heparin.

* * * * *